United States Patent [19]
Welchel et al.

[11] Patent Number: 6,022,818
[45] Date of Patent: Feb. 8, 2000

[54] HYDROENTANGLED NONWOVEN COMPOSITES

[75] Inventors: Debra Nell Welchel; Eric Scott Kepner, both of Woodstock; Crystal Sutphin Leach, Roswell, all of Ga.

[73] Assignee: Kimberly-Clark Worldwide, Inc., Neenah, Wis.

[21] Appl. No.: 08/627,837

[22] Filed: Apr. 2, 1996

Related U.S. Application Data

[63] Continuation of application No. 08/481,971, Jun. 7, 1995, abandoned.

[51] Int. Cl.[7] .............................. A61F 13/46; B32B 5/08; B32B 5/26; B32B 5/30
[52] U.S. Cl. ......................... 442/384; 15/209.1; 28/104; 28/105; 442/389; 442/408; 442/415; 442/417; 604/374; 604/378
[58] Field of Search ..................... 28/104, 105; 604/378, 604/374; 15/209.1; 442/384, 389, 408, 415, 417

[56] References Cited

U.S. PATENT DOCUMENTS

| | | | |
|---|---|---|---|
| 2,666,369 | 1/1954 | Niks ............................................. | 92/38 |
| 3,073,735 | 1/1963 | Till et al. .................................... | 156/38 |
| 3,379,811 | 4/1968 | Hartmann et al. ....................... | 264/210 |
| 3,485,706 | 12/1969 | Evans ........................................ | 161/72 |
| 3,676,242 | 7/1972 | Prentice .................................. | 156/62.4 |
| 3,692,618 | 9/1972 | Dorschner et al. ........................ | 161/72 |
| 3,755,527 | 8/1973 | Keller et al. .............................. | 264/210 |
| 3,821,068 | 6/1974 | Shaw ........................................ | 162/111 |
| 3,825,379 | 7/1974 | Lohkamp et al. ......................... | 425/72 |
| 3,825,380 | 7/1974 | Harding et al. ............................ | 425/72 |
| 3,837,995 | 9/1974 | Floden ..................................... | 161/150 |
| 3,849,241 | 11/1974 | Butin et al. ................................ | 161/169 |
| 3,942,723 | 3/1976 | Langdon .................................. | 239/135 |
| 3,954,361 | 5/1976 | Page ....................................... | 425/72 S |
| 3,970,417 | 7/1976 | Page ....................................... | 425/72 S |

(List continued on next page.)

FOREIGN PATENT DOCUMENTS

| | | | |
|---|---|---|---|
| 841938 | 5/1970 | Canada ...................................... | 92/11 |
| 0128667A2 | 12/1984 | European Pat. Off. ......... | D04H 1/44 |
| 0220640A2 | 5/1987 | European Pat. Off. ......... | D04H 1/56 |
| 0 235 309 | 9/1987 | European Pat. Off. ......... | A61F 13/18 |
| 0240009A2 | 10/1987 | European Pat. Off. ......... | C11D 17/04 |
| 0 308 320 | 3/1989 | European Pat. Off. ....... | D04H 13/00 |
| 0 492 554 | 7/1992 | European Pat. Off. ......... | D04H 1/44 |
| 0 540 041 | 5/1993 | European Pat. Off. ........ | A61L 15/60 |
| 0 577 156 | 5/1994 | European Pat. Off. ....... | D04H 13/00 |
| 0625602A1 | 11/1994 | European Pat. Off. ......... | D04H 1/46 |
| 91/10413 | 7/1991 | WIPO ............................... | A61F 5/44 |
| 94/29505 | 12/1994 | WIPO .............................. | D04H 1/44 |
| 96/07783 | 3/1996 | WIPO ........................... | D04H 13/00 |

OTHER PUBLICATIONS

JP 03 231 662 A (Kanae:KK) Oct. 15, 1991 & Database WPI Section Ch, Week 9148 Derwent Publications Ltd., London, GB; Class D22, AN 91–348765 See Abstract.
JP 04 289 257 A (UNI Carm Corp) Oct. 14, 1992 & Database WPI Section Ch, Week 9248 Derwent Publications Ltd., London, GB; Class A94, AN 92–392445 See Abstract.
Bernard M. Lichstein, "Demand Wettability, A New Method For Measuring Absorbency Characteristics of Fabrics", 1974, pp. 129–142.

*Primary Examiner*—James C. Cannon
*Attorney, Agent, or Firm*—James B. Robinson; Nicholas N. Leach

[57] ABSTRACT

Disclosed herein is an entangled nonwoven composite made from absorbent fibers such as wood pulp fibers and matrix fibers such as polyolefin staple fibers. The absorbent fibers are entangled with the matrix fibers in such a manner so that the composite has an absorbent-rich side and a matrix-rich side. Intermediate the two exterior sides there is an entangled interior portion made from a mixture of the absorbent and matrix fibers. The composite is particularly well-suited for use in multifunctional handling of fluids such as, for example, body fluids which are absorbed by personal care absorbent articles. The matrix fiber portion of the composite acts as a fluid intake region while the absorbent fiber portion acts as a fluid retention region and the portion of the composite intermediate the two exterior surfaces acts as a fluid transfer region.

12 Claims, 7 Drawing Sheets

U.S. PATENT DOCUMENTS

| | | | |
|---|---|---|---|
| 3,971,373 | 7/1976 | Braun | 128/146.2 |
| 3,985,481 | 10/1976 | Brackmann et al. | 425/72 S |
| 4,043,739 | 8/1977 | Appel | 425/461 |
| 4,047,861 | 9/1977 | Balaz | 425/7 |
| 4,073,850 | 2/1978 | Brackmann et al. | 264/93 |
| 4,100,324 | 7/1978 | Anderson et al. | 428/288 |
| 4,118,531 | 10/1978 | Hauser | 428/224 |
| 4,287,251 | 9/1981 | King et al. | 428/198 |
| 4,295,809 | 10/1981 | Mikami et al. | 425/72 S |
| 4,338,366 | 7/1982 | Evans et al. | 428/76 |
| 4,340,563 | 7/1982 | Appel et al. | 264/518 |
| 4,355,066 | 10/1982 | Newman | 428/198 |
| 4,426,417 | 1/1984 | Meitner et al. | 428/195 |
| 4,429,001 | 1/1984 | Kolpin et al. | 428/283 |
| 4,461,621 | 7/1984 | Karami et al. | 604/368 |
| 4,486,161 | 12/1984 | Middleton | 425/7 |
| 4,526,733 | 7/1985 | Lau | 264/12 |
| 4,604,313 | 8/1986 | McFarland et al. | 428/172 |
| 4,650,479 | 3/1987 | Insley | 604/358 |
| 4,655,757 | 4/1987 | McFarland et al. | 604/366 |
| 4,720,252 | 1/1988 | Appel et al. | 425/80.1 |
| 4,724,114 | 2/1988 | McFarland et al. | 264/510 |
| 4,773,903 | 9/1988 | Weisman et al. | 604/368 |
| 4,774,125 | 9/1988 | McAmish | 428/198 |
| 4,784,892 | 11/1988 | Storey et al. | 428/172 |
| 4,808,467 | 2/1989 | Suskind et al. | 428/284 |
| 4,818,464 | 4/1989 | Lau | 264/510 |
| 4,826,415 | 5/1989 | Mende | 425/722 |
| 4,826,498 | 5/1989 | Koczab | 604/383 |
| 4,834,735 | 5/1989 | Alemany et al. | 604/368 |
| 4,889,476 | 12/1989 | Buehning | 425/72.2 |
| 4,927,582 | 5/1990 | Bryson | 264/113 |
| 4,986,743 | 1/1991 | Buehning | 425/7 |
| 5,017,112 | 5/1991 | Mende et al. | 425/72.2 |
| 5,047,023 | 9/1991 | Berg | 604/368 |
| 5,137,600 | 8/1992 | Barnes et al. | 162/115 |
| 5,284,703 | 2/1994 | Everhart et al. | 428/283 |
| 5,328,759 | 7/1994 | McCormack et al. | 428/283 |
| 5,350,624 | 9/1994 | Georger et al. | 428/219 |
| 5,364,382 | 11/1994 | Latimer et al. | 604/378 |
| 5,382,400 | 1/1995 | Pike et al. | 264/168 |

HYDROENTANGLED NONWOVEN COMPOSITES

This application is a continuation of application Ser. No. 08/481,971 entitled "HYDROENTANGLED NONWOVEN COMPOSITES" and filed in the U.S. Patent and Trademark Office on Jun. 7, 1995, and now abandoned. The entirety of this application is hereby incorporated by reference.

FIELD OF THE INVENTION

The present invention is directed to entangled fibrous nonwoven webs. More particularly, the present invention is directed to hydroentangled structures which utilize absorbent fibers such as pulp fibers on one surface of the structures and matrix fibers such as polyolefin staple fibers on the other surface of the structures. The resultant composites have a wide variety of uses not the least of which is as a fluid management component in personal care absorbent articles such as diapers, training pants, incontinence garments, feminine hygiene products, bandages, wipes and the like.

BACKGROUND OF THE INVENTION

Fibrous nonwoven structures are used in a wide variety of applications, including but not limited to absorbent structures. Examples of such absorbent structures include personal care absorbent articles which are used to absorb such body fluids as urine and menses. As personal care absorbent articles have advanced in design, they have become increasingly more complex both in the number of components they contain and the very specific functions that they perform. Originally most if not all of these products were quite simple in design. Typically they included some type of body side liner, a simple absorbent core composed of wood pulp fluff and a garment side backing sheet or barrier such as a layer of plastic film. Many of these products were quite bulky due to what is now known to be their ineffective structural designs. Poor functional ability was often compensated for simply by enlarging the products such as by adding more absorbent. Very little was known about each of the components, their advantages, limitations and how they interacted with one another.

Today, a major emphasis has been on the reduction in size of these products. Diapers and feminine hygiene products such as sanitary napkins are but two examples of where a reduction in thickness has been a driving force in design criteria. Feminine hygiene products such as pantiliners are, in a relative sense, new products which have been made possible by the ability to reduce the size of the overall product. In so doing, maximum utilization of each and every component has become essential in the design of these products. The present invention is directed to such endeavors.

With respect to the ability of personal care absorbent articles to manage fluid intake and storage, low density fluid intake materials such as through air bonded carded webs have shown excellent uptake and temporary reservoir functions. They lack, however, an effective retention and storage mechanism such as can be supplied by cellulose or cellulosic components such as wood pulp fibers, also referred to as fluff. There are alternatives for addressing this deficiency such as adding retention components to the intake material or layering an intake material with a retention material within a product structure.

The addition of a retention component to the structure creates a mixture of intake and retention functions and properties. While this can be an effective structure, in some instances it is desirable to separate functions to maximize performance in a personal care product. For instance, if the lofty structure is intended as a body side liner, then the addition of cellulose may increase the amount of flowback from the liner onto the user's skin. This is clearly not a desired function and therefore should be avoided.

Another alternative is to layer or ply the retention material with the fluid intake layer. This eliminates cellulose in the body side portion of the composite but creates difficulties with regard to the interface between the intake and retention portions of the composite. Failure at this interface can cause several problems in the system including lack of durability in the physical structure and failure of fluid pathways due to insufficient communication between the two layers. The layers can be held together through any number of attachment means, including adhesive bonds and thermal bonds. Thermal bonding requires a thermoplastic component in each layer. Consequently, a substrate which is made entirely from cellulose will not be thermally bondable. Adhesive bonding can be used to attach the layers, but adhesives can impede the creation of fluid pathways between the intake and retention surfaces. Mechanical bonding, such as hydroentangling or needling, can be used to create structures with the desired level of attachment between the plies and with fluid pathways. Each method of attachment has been found to give different properties to the resultant structure. The present invention focuses on the use of entangling techniques to create a composite with specific desired properties. A further understanding of the present invention can be gained by a review of the following specification, drawings and claims.

SUMMARY OF THE INVENTION

The present invention is directed to a fibrous nonwoven composite which is formed from at least two fibers sources which are subsequently entangled with one another such as, for example, by hydroentangling. One source of fibers used in the composites of the present invention is absorbent fibers such as wood pulp fibers which are capable of absorbing fluids such as urine and menses. Other absorbent fibers are also contemplated to be within the scope of the present invention. The other source of fibers is fibers which are collectively referred to as matrix fibers. They are often less absorptive than the pulp fibers as their function is to take in fluids, temporarily hold them and then transfer them to the absorbent fibers. Examples of matrix fibers include, but are not limited to, hydrophilic fibers and hydrophobic fibers which if desired may be treated to be hydrophilic. The matrix fibers are typically staple or continuous fibers made from extrudable and spinnable polymers such as for example, rayon, polyolefins and polyesters. In addition, the matrix fibers may include several types of fibers such as blends of polyolefin fibers and polyester fibers.

To form the entangled composite, separate webs of absorbent and matrix fibers are formed, brought together and then entangled with one another. The degree of entanglement is controlled so as to prevent complete integration of the fibers from the two webs. As a result, one side of the composite is essentially absorbent fibers while the other side of the composite is essentially matrix fibers. The matrix fibers are selected so as to permit rapid intake of fluids such as urine and menses while the absorbent fibers serve to absorb and retain the fluids taken in by the matrix fibers. By avoiding complete integration of the two fiber sources, the matrix fibers create a bodyfacing fluid intake exterior surface to the composite which is suitable for positioning toward or in contact with the wearer's body. Since there are essentially no absorbent fibers at this surface, a much drier feeling surface is created. Conversely, because the opposite surface, the fluid retention exterior surface, of the composite is essentially absorbent fibers, maximum absorption and retention is provided by this side of the product. In between the two exterior surfaces an interface is created where the absorbent fibers mix with the matrix fibers thereby creating a fluid transfer zone which, due to the entangling, maximizes the transfer of fluid from the matrix fibers into the absorbent fibers. In addition, because there is no adhesive used, there is believed to be less interference at the interface.

The composite so formed has particular utility as an absorbent mechanism for personal care absorbent articles such as diapers, training pants, incontinence devices, feminine hygiene products, wipers, bandages and the like. In the area of feminine hygiene products, the material of the present invention is particularly well-suited as a pantiliner material. Depending on the fibers and layers used as the matrix portion of the composite, a material can be developed which has a soft exterior side suitable for use against the skin and an opposite surface which readily retains liquid. Alternatively, the composite can be used underneath a conventional body side liner material to form yet another version of a finished product.

The entangled nonwoven composites according to the present invention should include from about 20 to about 75 percent by weight absorbent fibers and from about 25 to about 80 percent by weight matrix fibers based upon the total weight of the composite and in more refined embodiments can include from about 50 to about 60 percent absorbent fibers and about 40 to about 50 percent matrix fibers. The fluid intake exterior surface should comprise essentially matrix fibers, the interior portion should contain a mixture of the absorbent fibers and matrix fibers entangled with one another and the fluid retention exterior surface should contain essentially absorbent fibers. If desired, the absorbent fibers may contain a wet strength and/or a superabsorbent admixed therewith. The resultant composite should have a fluid intake rate of about 2 cubic centimeters per minute or greater, a cohesion value of about 1.5 kilograms or greater, a cup crush value of about 1000 grams or less and a demand absorbency rate of one gram per minute or greater.

Variations to the composite may also be employed as, for example, by adding an additional layer to the composite such as a second top sheet positioned adjacent to and in contact with the fluid intake exterior surface of the top sheet. This second top sheet may comprise a fibrous nonwoven web which itself may include a plurality of matrix fibers.

The composites of the present invention may be used in a wide variety of applications including, but not limited to, personal care absorbent articles such as, for example, pantiliners. The design of such articles will include at a minimum, a backing sheet and an absorbent core. The composites of the of the present invention may be used as the absorbent core in which case the fluid retention exterior surface of the composite will be positioned toward the backing sheet. As result, the fluid intake exterior surface can be positioned adjacent the wearer's skin. Alternatively, where the composite includes a second top sheet, the second top sheet will be positioned adjacent the wearer's skin.

BRIEF DESCRIPTION OF THE DRAWINGS

FIG. 7 is a photomicrograph of the material according to the present invention as described in Example 2a.

FIG. 8 is a photomicrograph of the material according to the present invention as described in Example 3a.

DETAILED DESCRIPTION OF THE INVENTION

Figure 1:
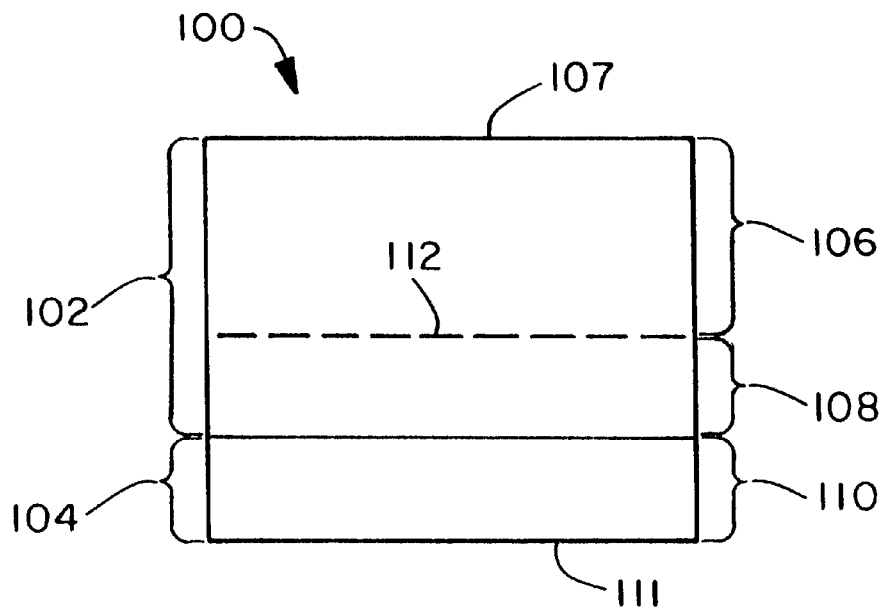
FIG. 1 is a cross-sectional side view of an entangled absorbent and matrix fiber composite according to the present invention.
Figure 3:
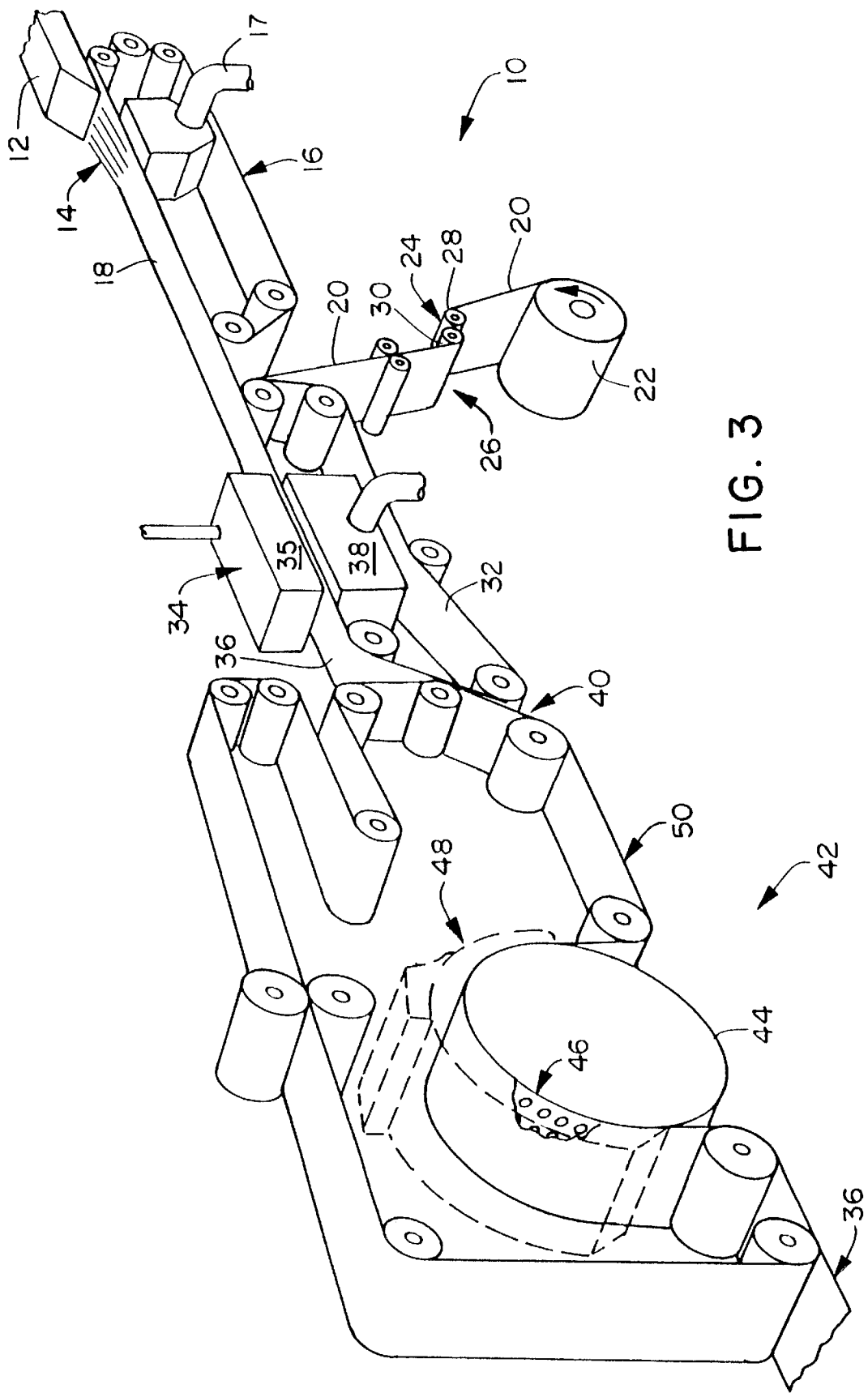
FIG. 3 is a schematic side view of a process for forming an entangled absorbent and matrix fiber composite according to the present invention. The equipment in this figure includes a hydroentangling apparatus.

Turning to FIG. 1 there is shown in cross-section, an entangled absorbent fiber and matrix fiber composite according to the present invention. The composite 100 is formed from two layers of material including a top sheet 102 and a bottom sheet 104. The top sheet 102 is formed from a fibrous nonwoven web made from or including matrix fibers and the bottom sheet 104 is formed from a layer of absorbent fibers. As used herein, "absorbent fibers" is meant to include both natural and synthetic cellulosic and cellulose derivative fibers. Examples of such fibers include, but are not limited to, wood pulp fibers, rayon fibers, flax fibers, eucalyptus fibers, cotton fibers and the like. For purposes of the present invention, "absorbent fibers" and "pulp fibers" shall be used interchangeably and shall have the same meaning and scope. The two layers are positioned one on top of the other and then entangled together via a process such as is shown in FIG. 3 and described below. In this process the absorbent fibers are integrated into the matrix fibers through the use of water jets. Due to the entangling of the absorbent fibers with the matrix fibers at the interface between the two sheets, the composite has three variable regions 106, 108 and 110 as shown in FIG. 1. The first exterior region 106 includes a fluid intake exterior surface 107 and it, along with the first exterior region as a whole, are composed essentially of the fibers from the matrix layer or top sheet 102. By "essentially" it is meant that the weight percent of the matrix fibers, based upon the total weight of the fibers in region 106 will be greater than or equal to about 90 percent. In the interior region 108, which is formed by the interface between sheets 102/104 and an imaginary line 112 selectively drawn through the top sheet 102, there will be a mixture of fibers from both the top sheet 102 and the bottom sheet 104. The second exterior region 110 includes a fluid retention exterior surface 111 and it, along with the second exterior region 110 as a whole, are composed essentially of the absorbent fibers from the absorbent sheet 104. By "essentially" it is meant that the weight percent of the absorbent fibers, based upon the total weight of the fibers in region 110, will be greater than or equal to about 90 percent. The size of the regions 106, 108 and 110 depend on the degree of hydroentangling. As hydroentangling increases, region 108 will increase and regions 106 and 110 will decrease. As a result of the entanglement, the composite will include from about 20 to about 75 percent by weight absorbent fibers and from about 25 to about 80 percent by weight matrix fibers based upon the total weight of the composite 100. In certain, more refined embodiments, the composite 100 will include from about 50 to about 60 percent absorbent fibers and about 40 to about 50 percent matrix fibers based upon the total weight of the composite.

The first exterior region 106 serves as a fluid intake region while the interior region 108 serves as a fluid transfer region and the second exterior region 110 serves as a fluid retention region. When the material of the present invention is used as, for example, a personal care absorbent article such as a pantiliner, body fluids such as blood and menses will enter the fluid intake region 106 through the fluid intake exterior surface 107. This surface and region are comprised of the matrix fibers which are less hydrophilic than the absorbent fibers. As a result, the fluid will want to quickly pass through to another region in the material which, in this case, is the fluid transfer region 108. In this region there is a mixture of matrix fibers and absorbent fibers. As a result, this region will have a higher affinity for absorbed fluids but not the affinity of the absorbent-rich fluid retention region 110. This in turn creates a driving force for the fluid. The fluid is pulled into this region by the absorbent fibers but the matrix fibers keep the absorbent fibers somewhat apart which still gives the structure in this area a more open structure. Once the fluid has been pulled into the fluid transfer region, the high concentration of absorbent fibers in the fluid retention region 110 act to draw the fluid in so that the fluid can be stored away from the user.

Figure 2:
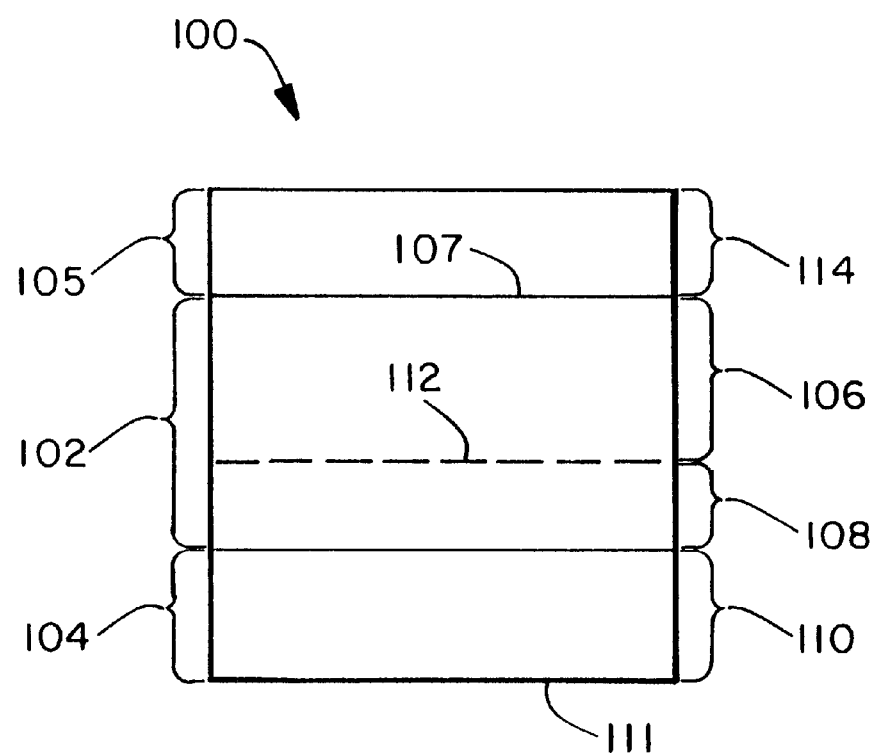
FIG. 2 is a cross-sectional side view of another entangled absorbent and matrix fiber composite according to the present invention. In this embodiment, the top portion of the composite is a two layer material which provides dual functionality.

Another embodiment of the composite is shown in FIG. 2 of the drawings. In this configuration, the composite 100 is formed from three layers of material including the same top sheet 102 and a bottom sheet 104 as in FIG. 1 and a second top sheet 105 disposed on a side 107 of the top sheet 102 which is opposed to the bottom sheet 104. As with the previous embodiment, the top sheet 102 is formed from a layer of matrix fibers, the bottom sheet 104 is formed from a layer of absorbent fibers and the second top sheet 105 is formed from a fibrous nonwoven web which may include matrix fibers. An advantageous embodiment is where the top sheet 102 and the second top sheet 105 contain bicomponent matrix fibers so that they can be subjected to a heating process to bond the two sheets together. The fibers of the top sheet 102 and the bottom sheet 104 are entangled together in the same manner as described above. As with the embodiment shown in FIG. 1 and described above, due to the entangling of the fibers from the bottom sheet 104 into the top sheet 102, region 106 will contain essentially matrix fibers. Region 108 will be a mixture of absorbent fibers and nonwoven matrix fibers and region 110 will contain essentially absorbent fibers. In addition, there will be yet a third region 114 formed by the second top sheet 105 which will also contain essentially matrix fibers. These matrix fibers may be the same as or different than the matrix fibers in region 106 or they may be a blend of matrix fibers.

The second top sheet 105 can be designed to be aesthetically more pleasing to the touch and therefore more comfortable to the user. This can be accomplished by forming the second top sheet 105 from fibers which have a smaller diameter and/or denier than the fibers of the top sheet 102.

Turning to FIG. 3 of the drawings there is shown in schematic form a process and apparatus 10 for forming entangled nonwoven composites according to the present invention. According to the present invention, a dilute suspension of absorbent fibers, in this case wood pulp fibers, is supplied by a head-box 12 and deposited via a sluice 14 in a uniform dispersion onto a forming surface 16 of a conventional paper making machine. The suspension of pulp fibers may be diluted to any consistency which is typically used in conventional paper making processes. For example, the suspension may contain from about 0.05 to about 0.5 percent by weight pulp fibers suspended in water to form a slurry. In addition, a chemical debonder may be added to the slurry to further facilitate the process. The slurry is laid down on the forming surface 16 and a vacuum assist 17 is used to pull the water out of the deposited fibers thereby creating a pulp sheet 18.

The pulp fibers may be any high-average fiber length pulp, low-average fiber length pulp or mixtures of the two types of fibers. The high-average fiber length pulp fibers will typically have average fiber lengths from about 1.5 millimeters (mm) to about 6 millimeters. Exemplary high-average fiber length wood pulp fibers include those available from the Kimberly-Clark Corporation under the trade designations Longlac 19, Coosa River 54 and Coosa River 56.

The low-average fiber length pulp fibers may be, for example, certain virgin hardwood pulps and secondary pulps (recycled) from sources such as, for example, newsprint, reclaimed paperboard and office waste. The low-average fiber length pulp fibers typically have an average fiber length of less than about 1.2 mm and more typically in the range of about 0.7 to about 1.2 mm. An exemplary low-average fiber length fiber is available from Kimberly-Clark Corporation under the trade designation Coosa River 57.

Mixtures of high-average and low-average fiber length pulp fibers may contain varying proportions of the two types of fibers. Generally they can contain from about 20 to about 100 percent high-average length fibers and from about 0 to about 80 percent low-average length fibers on a weight percent basis based upon the total weight of all the fibers. It is also possible to use all of just one type of fiber although this would make processing more difficult as with, for example, 100 percent low-average length fibers.

The pulp fibers used in conjunction with the present invention may be unrefined or may be beaten to varying degrees of refinement. Small amounts of wet-strength resins and/or resin binders may be added to improve strength and abrasion resistance. Useful binders and wet-strength resins include, but are not limited to, Kymene 557 H resin available from the Hercules Chemical Company and Parez 631 resin which is available from American Cyanamid, Inc. Cross-linking agents and/or hydrating agents may also be added to the pulp mixture to reduce the degree of hydrogen bonding if a very open or loose nonwoven pulp fiber web is desired. One exemplary debonding agent is available from the Quaker Chemical Company of Conshohocken, Pa. under the trade designation Quaker 2008. Another debonding agent is available from Witco/Sherex Chemical Company, Inc. of Dublin, Ohio under the trade designation Arosurf PA727. The addition of certain debonding agents in an amount of, for example, about 1 to about 4 percent by weight of the pulp sheet appears to reduce the measured static and dynamic coefficients of friction and improves the abrasion resistance of the non-pulp side of the composite fabric. The debonding agent is believed to act as a lubricant or friction reducer.

Returning to the process shown in FIG. 3 of the drawings, a fibrous nonwoven web substrate 20 is unwound from a supply roll 22 and travels in the direction indicated by the arrow associated therewith. The nonwoven substrate 20 optionally may be passed through a nip 24 of an S-roll arrangement 26 formed by the stack rollers 28 and 30.

The nonwoven substrate 20 may be formed from known continuous and noncontinuous filament or fiber nonwoven extrusion processes. Examples of continuous fiber nonwoven extrusion processes include, but are not limited to, known solvent spinning or meltspinning processes such as, for example a spunbonding process. See for example U.S. Pat. No. 3,692,618 to Dorschner et al., U.S. Pat. No. 4,340,563 to Appel et al. and U.S. Pat. No. 5,382,400 to Strack et al. which are incorporated herein by reference in their entirety. Examples of known noncontinuous fiber nonwoven extrusion processes include those which use pre-formed staple length fibers such as bonded carded web forming processes. Of particular use with the present invention are known processes for forming through-air bonded carded webs. These processes may be utilized in-line or the substrate 20 be formed off-line and then brought into the present process as in the form of the supply roll 22 shown in FIG. 3.

Bonded carded webs are made from staple fibers which are usually purchased in bales. The bales are placed in a picker which separates the fibers. Next, the fibers are sent through a combing or carding unit which further breaks apart and aligns the staple fibers in the machine direction so as to form a machine direction-oriented fibrous nonwoven web. Once the web has been formed, it is then bonded by one or more of several bonding methods. One bonding method is powder bonding wherein a powdered adhesive is distributed throughout the web and then activated, usually by heating the web and adhesive with hot air. Another bonding method is pattern bonding wherein heated calendar rolls or ultrasonic bonding equipment is used to bond the fibers together, usually in a localized bond pattern though the web can be bonded across its entire surface if so desired. The best method though, when using bicomponent staple fibers is to use a through-air bonder such as is described above with respect to the bicomponent spunbond web formation process. In order to maintain the lofty and open nature of the resultant fibrous nonwoven web according to the present invention, the bonding process used to bond the fibers of the fibrous nonwoven web together should be a process such as through-air bonding which does not unduly compress or collapse the structure during the formation process. In through-air bonding, heated air is forced through the web to melt and bond together the fibers at their crossover points. Typically the unbonded web is supported on a forming wire or drum. In addition a vacuum may be pulled through the web if so desired to further contain the fibrous web during the bonding process. Such through-air bonding processes are well known and therefore need not be described herein in detail.

Airlaying is another well known process by which fibrous nonwoven webs according to the present invention can be made. In the airlaying process, bundles of small fibers usually having lengths ranging between about 6 and about 19 millimeters are separated and entrained in an air supply and then deposited onto a forming screen, oftentimes with the assistance of a vacuum supply. The randomly deposited fibers are then bonded to one another using, for example, hot air or a spray adhesive.

Bonding processes such as point bonding and pattern bonding using smooth and/or pattern bonding rolls may create a resultant fibrous nonwoven web which is too dense and does not have the degree of voids necessary for the present invention. Whatever process is chosen, the degree of bonding will be dependent upon the fibers/polymers chosen but, in any event, it is desirable that there be as little compression as possible during the heating stage.

The pulp fiber layer 18 and the nonwoven substrate 20 are brought together upon a foraminous entangling surface 32 which passes through a conventional hydraulic entangling machine 34 which includes hydraulic entangling manifolds 35. It is desirable that the pulp layer 18 be positioned between the nonwoven substrate 20 and the hydraulic entangling manifolds 35. As the pulp layer 18 and nonwoven substrate 20 pass through the machine 34, they are treated with jets of liquid which force the pulp fibers into the matrix fibers of the nonwoven substrate 20 thereby entangling the pulp fibers with the nonwoven matrix fibers to form the entangled pulp and nonwoven composite 36 of the present invention.

The hydraulic entangling may be accomplished utilizing conventional hydraulic entangling equipment such as may be found in, for example, U.S. Pat. No. 3,485,706 to Evans and U.S. Pat. No. 5,284,703 to Everhart et al. both of which are incorporated herein by reference in their entirety. The hydraulic entangling may be carried out with any appropriate working fluid such as, for example, water. The working fluid flows through one or more manifolds 35 which evenly distribute the fluid to a series of individual holes or orifices. The holes or orifices may be from about 0.003 to about 0.015 inches (0.076 to 0.38 millimeters) in diameter. For example, the invention may be practiced utilizing a manifold produced by Honeycomb Systems, Inc. of Biddeford, Me. containing a single row of aligned holes (30 holes per inch/12 holes per centimeter) with each hole having a diameter of 0.007 inches (0.18 millimeters). In the process used to form the examples of the present invention, three to four manifolds of the type just described were aligned in sequence across the traveling layers 18 and 20.

In the hydraulic entangling process the working fluid passes through the orifices at a pressure ranging from about 200 to about 2000 pounds per square inch gage (psig) (about 1379 kilopascals to about 13,790 kilopascals). An important feature of the present invention is that there not be complete integration of the pulp fibers into the matrix fibers of the nonwoven layer or substrate 20. As a result, it will be necessary to adjust both the pressure and the line speed of the process to achieve the desired limited degree of integration. Also, the number of manifolds 35 and the pressure within each manifold will affect the degree of integration as will the basis weight of the nonwoven substrate into which the pulp fibers are integrated.

The fluid impacts the pulp fiber layer 18 and the nonwoven substrate 20, both of which are supported by a foraminous surface 32 which may be, for example, a single plane mesh wire having a mesh size of from about 40×40 strands per inch (15.7×15.7 strands per centimeter) to about 100×100 strands per inch (39.4×39.4 strands per centimeter). The foraminous surface 32 also may be a multi-ply mesh having a mesh size from about 50×50 to about 200×200 strands per inch (19.7×19.7 to about 78.7× 78.7 strands per centimeter). As is typical in many water jet treatment processes, vacuum slots 38 may be located directly beneath the hydro-needling manifolds 35 or beneath the foraminous entangling surface 32 downstream of the manifolds 35 so that excess water can be withdrawn from the entangled composite material 36.

After the fluid jet treatment, the composite material or fabric 36 may be transferred to a non-compressive drying operation or a compressive drying operation such as steam cans (not shown). A differential speed pick-up roll 40 may be used to transfer the material from the hydraulic needling belt to a non-compressive drying operation. Alternatively, conventional vacuum-type pick-ups and transfer fabrics may be used. If desired, the composite fabric may be wet creped before being transferred to the drying operation. Non-compressive drying of the web may be accomplished utilizing a conventional rotary drum through-air dryer 42. The through-air dryer 42 may be an outer rotatable cylinder 44 with perforations 46 in combination with an outer hood 48 for receiving hot air blown through the perforations 46. A through-dryer belt 50 carries the composite fabric 36 over the upper portion of the through-dryer outer cylinder 44. The heated air forced through the perforations 46 in the outer cylinder 44 of the through-dryer 42 removes water from the composite fabric 36. The temperature of the air forced through the composite fabric 36 by the through-dryer 42 may range from about 93° Celsius (C.) to about 260° C. (200° F. to about 500° F.). Other useful through-drying methods and apparatus may be found in, for example, U.S. Pat. Nos. 2,666,369 and 3,821,068 both of which are incorporated herein by reference in their entirety.

It may be desirable to use finishing steps and/or post treatment processes to impart selected properties to the composite fabric 36. For example, the fabric may be lightly pressed by calendar rolls, creped or brushed to provide a uniform exterior appearance and/or certain tactile properties. Alternatively, and/or additionally, chemical post-treatments such as surfactants, adhesives or dyes may be added to the fabric.

In one aspect of the invention, the fabric may contain various materials such as, for example, activated charcoal, clays, starches, and superabsorbent materials. For example, these materials may be added to the suspension of pulp fibers used to form the pulp fiber layer. These materials may also be deposited on the pulp fiber layer prior to the fluid jet treatments so that they become incorporated into the composite fabric 36 by the action of the fluid jets. Alternatively and/or additionally, these materials may be added to the composite fabric after the fluid jet treatments. If superabsorbent materials are added to the suspension of pulp fibers in the pulp fiber layer before water-jet treatment, it is preferred that the superabsorbents are those which can remain inactive during the wet-forming and/or water jet treatment steps and which can be activated later. Conventional superabsorbents may be added to the composite fabric after the water-jet treatment. See for example U.S. Pat. No. 5,328,759 to McCormack et al. which is incorporated herein by reference in its entirety. Useful superabsorbents include, for example, a sodium polyacrylate superabsorbent available from the Hoechst Celanese Corporation under the trade designation Sanwet IM-5000 P. Superabsorbents may be present at a proportion of up to about 50 grams of superabsorbent per 100 grams of pulp fiber. They may be used in various forms including, for example, particles, flakes and fibers.

Having described the materials and process of the present invention in detail, several examples were prepared to demonstrate the present invention. These examples as well as the test procedures to measure them are set forth below.

Test Procedures
Fluid Intake Time

The composite structures of the present invention were tested to determine how rapidly each would absorb 2 cubic centimeters of an artificial menstrual fluid. The formulation of the synthetic menstrual fluid is on a weight percent basis, approximately 82.5% water, 15.8% polyvinyl pyrrolidone and 1.7% salts, coloring agents, and surfactants. It has a viscosity of 17 centipoise, and a surface tension of 53.5 dynes per centimeter. The test utilizes a test apparatus which consisted of 1) a Lucites® block and 2) a flat, horizontal test surface.

Figure 4:
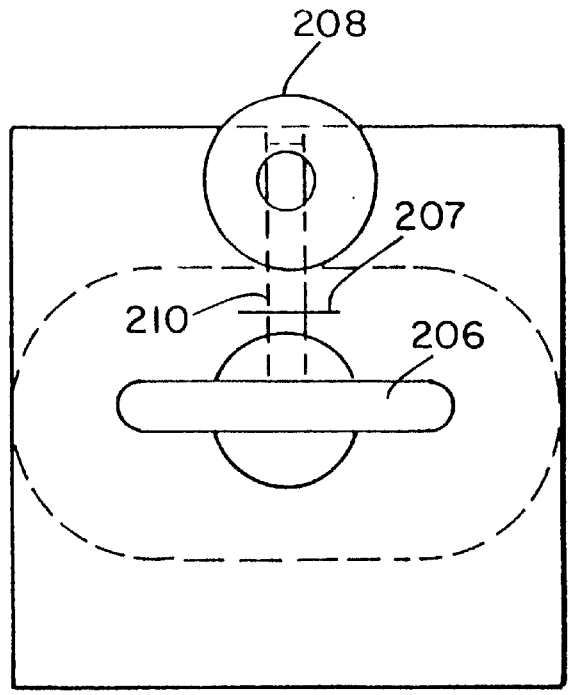
FIG. 4 is a top plan view of a test apparatus for measuring the rate at which an absorbent structure absorbs liquid.
Figure 5:
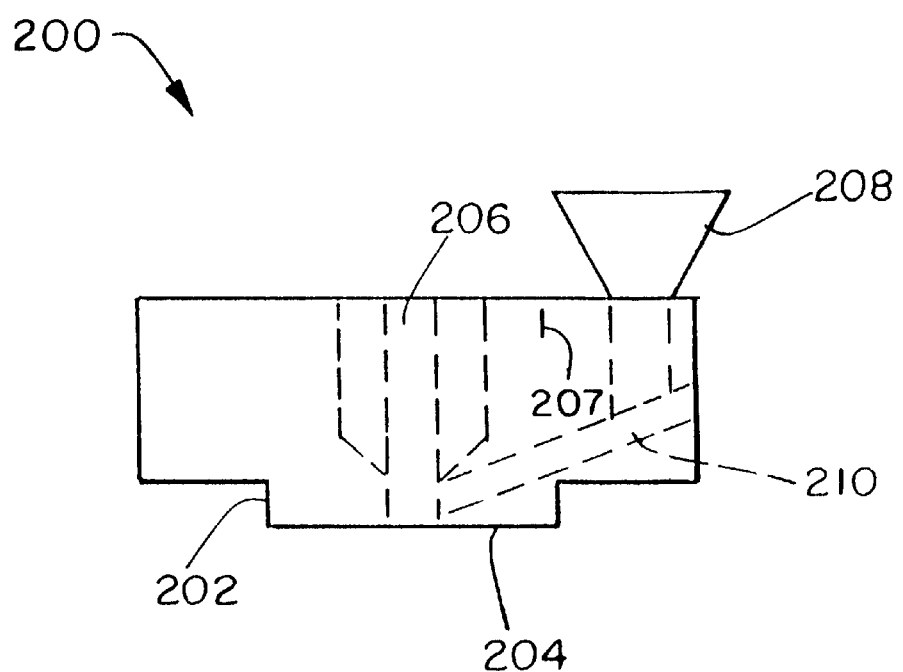
FIG. 5 is a cross-sectional view of a test apparatus for measuring the rate at which an absorbent structure absorbs liquid.

FIG. 4 is a plan view of the Lucite® block. FIG. 5 is a sectional side view of the Lucite® block. The block 200 has a base 202 which protrudes from the bottom of the block. The base 202 has a flat surface 204 which is approximately 2.875 inches (7.3 centimeters) long by 1.5 inches (3.8 centimeters) wide and which forms the bottom of the block 200. An oblong opening 206 (about 1.5 inches (3.8 cm) long by about 0.25 inches (0.64 cm) wide) is located in the center of the block and extends from the top of the block to the surface 204 of the base 202 of the block. When the bottom of the opening 206 is obstructed, the opening 206 can hold about 10 cubic centimeters of fluid. A mark 207 on the block 200 indicates a liquid level of about 2 cubic centimeters. A funnel 208 on the top of the block feeds into a passage 210 which is connected to the oblong opening 206. Fluid is poured down into funnel 208 and passes through the passage 210 into the oblong opening 206 and out onto a test sample underneath the block.

Each sample (7.6 cm×17.8 cm) was tested by placing it on a flat, acrylic, horizontal test surface and then puffing the flat, projecting base of the block on top of the sample (nonwoven side up/pulp side down) so that the long dimension of the oblong opening 206 was parallel to the long dimension of the sample and centered between the ends and sides of the sample. The weight of the block was about 163 grams so that the block rested on the sample with a pressure of about 7 grams per square centimeter. Approximately 4 cubic centimeters of the artificial menstrual fluid was dispensed into the funnel from a Repipet (catalogue No.13-687-20; Fischer Scientific Company). A stopwatch was started when the forward front of the liquid passed the mark 207. The fluid filled the oblong opening of the block and the watch was stopped when the trailing meniscus of the fluid passed the mark 207 thereby indicating that 2 cubic centimeters of fluid had been absorbed. The amount of time to absorb the 2 cubic centimeters of artificial menstrual fluid was then recorded. This value was then converted to cubic centimeters per minute. Ten repetitions were performed for each sample and an average was then calculated.

Cup Crush Test

The cup crush test was used to evaluate fabric stiffness by measuring the peak load required for a 4.5 centimeter diameter hemispherically-shaped foot to crush a 9.0 inch by 9.0 inch (22.9 centimeter by 22.9 centimeter) piece of fabric shaped into an approximately 6.5 centimeter diameter by 6.5 centimeter tall inverted cup while the cup shaped fabric was surrounded by an approximately 6.5 centimeter diameter cylinder to maintain a uniform deformation of the cup shaped fabric. The foot and cup were aligned to avoid contact between the cup walls and the foot which could affect the peak load. The peak load was measured while the foot was descending at a rate of about 0.25 inches per second (0.64 centimeters per second) which is equivalent to 15 inches per minute (38.1 centimeters per minute) utilizing a Model 3108-128 10 pound load cell (4.54 kg load cell) available from the MTS Systems Corporation of Cary, N.C. A total of seven to ten repetitions were performed for each material and then averaged to give the reported values.

Basis Weight

The basis weights for the samples were determined in accordance with Federal Test Method 191A/5041. Sample sizes were 9 inches by 9 inches (22.9 centimeters by 22.9 centimeters). A total of seven to ten samples were weighed and averaged.

Cohesion Test

The cohesion strength of the composite was measured by measuring the cohesion force between the two layers of the composite material. The minimum force required to separate the two layers was given in kilograms of force per square inch.

For each sample, the cohesion force of a one inch square (6.45 square centimeters) sample was measured using a Chatillon Digital Force Gauge Model DFI 50 from John Chatillon and Sons, Inc. of Greensboro, N.C. The device had a pneumatically operated base plate measuring 2 inches (5.1 cm) by 4 inches (10.2 cm) and a one inch (2.54 cm) square top plate which was connected to a digital force gauge. Double-faced adhesive tape was applied to both the base plate and the top plate and a 2 inch (5.1 cm) by 4 inch (10.2 cm) sample of material was positioned on top of the 2 inch by 4 inch base plate. The tape used to cover the surfaces of both the base plate and the top plate was Scotch® Brand double-coated pressure-sensitive tape number 406 which is available in 1-inch (2.54 cm) and 2-inch (5.1 cm) widths. The two inch wide tape was used for the base plate and the one inch wide tape was used for the top plate. Once the sample had been placed on top of the base plate (pulp side adjacent the base plate), the base plate and sample were compressed for a period of 3 seconds under a pressure of 60 pound per square inch gauge (414 kilopascals). After 3 seconds, the pressure was released. The digital force gauge was then activated and the sample was compressed between the base plate and top plate at 60 pounds per square inch gauge for a period of ten seconds. Next, the base plate was drawn away from the top plate and the separation force was measured in kilograms per square inch. The amount of force required to separate the composite was then recorded. Ten repetitions were performed for each sample and then averaged.

Demand Absorbency Test

Figure 6:
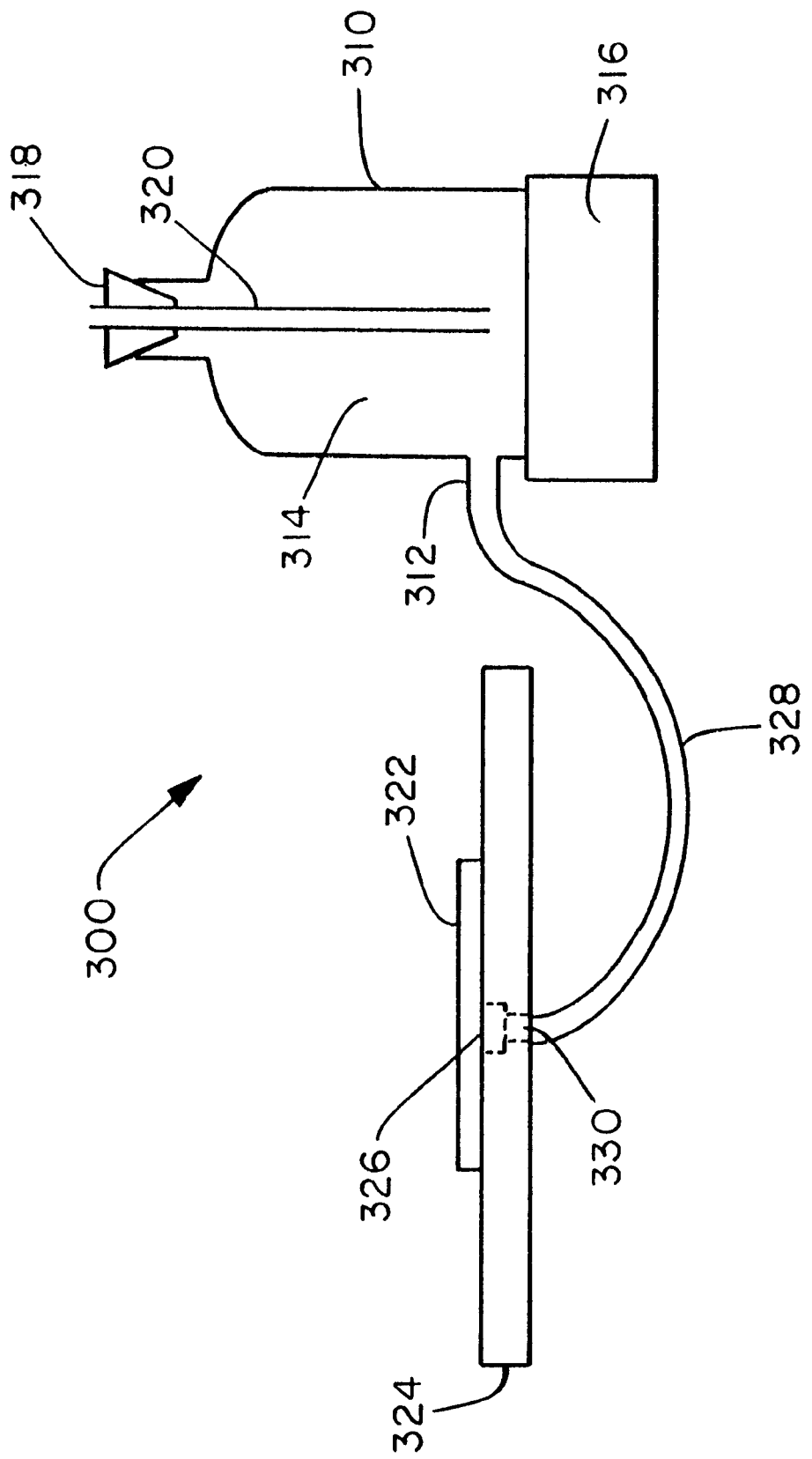
FIG. 6 is a side perspective view of a test apparatus for measuring demand absorbency of liquids by an absorbent structure.

The demand absorbency test measures the intake rate in grams per minute of an absorbent material at zero hydrostatic head (pressure). It was conducted in accordance with the test entitled "DEMAND WETTABILITY, A NEW METHOD FOR MEASURING ABSORBENCY CHARACTERISTICS OF FABRICS" written by Bernard M. Lichstein of the Johnson and Johnson Company of New Brunswick, N.J. 08903 which was given and published at the 1974 INDA Technical Symposium (pages 129 through 142). INDA (the Association of the Nonwoven Fabrics Industry) has offices at 1001 Winstead Drive, Suite 460, Cary, N.C. The test apparatus used in the present instance was different than that described in the above test. The actual test apparatus is shown in FIG. 6 of the drawings.

There were several changes to the apparatus described in the test procedure. Referring to FIG. 6, the test apparatus 300 included a 400 milliliter bottle 310 with a side exit hole 312. The bottle 310 was filled with the same synthetic menstrual fluid 314 as was described earlier and was placed on top of a Sartorius scale 316 model number 1413 mp8-1 to allow gram per unit time data to be recorded as the test samples drew fluid from the bottle and therefore reduced its weight. The top of the bottle 310 was plugged with a single hole rubber stopper 318. Through the hole in the stopper there was placed a 0.6 cm (OD) glass tube 320. The glass tube 320 was placed sufficiently deep within the bottle so as to ensure that its open bottom end remained submerged in the synthetic menstrual fluid 314 throughout the test. The rubber stopper/glass tube combination replaced the air bleed system described in the test procedure.

The sample materials 322 were positioned, nonwoven-rich side down, on top of a 12.7 centimeter by 22.9 centimeter acrylic plate 324 which had a 1.59 centimeter diameter hole 326 positioned in the middle of the top of the plate. The hole descends 0.5 cm before reducing in diameter to 1.0 cm and then descends an additional 0.8 cm. It then takes a right turn, then exits the side of the plate at hole 330. The bottle 310 was connected to the plate 324 using a Tygons plastic tube 328 having an inner diameter of 0.635 centimeters and a wall thickness of 0.159 centimeters. The tube 328 was fitted into a 0.95 centimeter diameter hole 330 in the side of the plate 324 which was in fluid communication with the plate hole 326. The samples which had dimensions of 17.6 centimeters by 7.6 centimeters were positioned on top of the plate 324 such that the each sample was centered over top of the plate hole 326 and the long dimension of the sample corresponded to the long dimension of the plate. No top plate was placed over the sample as described in the test procedure. As a result, the test samples were under no compressive force during the absorption of fluid.

To conduct the test, the operator should ensure that the submerged tip of the glass tube 320 and the top surface of the plate 324 are at the same elevation. As the sample 322 is placed over the hole 326 in the plate 324 and makes contact with the synthetic menstrual fluid, a stopwatch or other suitable timing device is started. As the fluid is absorbed into the test specimen, fluid is drawn out of the bottle and is replaced by air through the glass tube causing air bubbles to percolate up through the remaining fluid 314 in the bottle 310. The loss of fluid from the bottle 310 is shown on the scale 316 as a loss of mass. The time in seconds to reduce the weight on the scale by one gram is recorded as grams per number of seconds. This value is then multiplied by the conversion factor 60 seconds/one minute to yield the absorption rate in number of grams per minute. A total of 5 to 7 tests were run and averaged to yield the results reported below.

EXAMPLES

A series of five example materials were prepared as described below. With respect to Examples 1 through 4 there were three different embodiments tested. The "a" sample was a hydroentangled sample according to the present invention. The "b" sample was the component materials laid one on top of the other but with no attachment of the materials to one another. The "c" sample was the same two materials adhesively attached to one another. The adhesive used was 3M Super 77-N Spray Adhesive produced by the 3M Corporation of St. Paul, Minn. Add-on of the adhesive was between about 10 and about 25 grams per square meter. The samples in Examples 1, 2 and 4 utilized a single layer of nonwoven with a pulp sheet to form the composite while Example 3 utilized a two layer nonwoven and a pulp sheet to form the composite. Example 5 was a pulp sheet only. As a result, there were no samples a, b and c in Example 5. Intake rates were calculated for samples 1a, 2a, 3a, 4a and 5 only.

Example 1

In Example 1a, a two layer composite was formed using a bonded carded web and a pulp sheet. The bonded carded web was a through-air bonded carded web or TABCW. The web included on a weight percent basis based upon the total weight of the web: 40 percent 6.0 denier polyester staple fibers having a length of 38 millimeters and 60 percent 3.0 denier polyethylene sheath/polyester core bicomponent fibers having a length of 38 millimeters. The polyester fibers were obtained from the Hoechst Celanese Corporation of Spartanburg, S.C. The bicomponent fibers were obtained from the BASF Wyandotte Corporation of Parsippany, N.J. and were designated as being from merge 1-1039.

The fibers were all sent through an opener and were uniformly mixed together before being carded into a web. Once the web was formed, it was then sent through a through-air bonder with an air temperature of 135° C. The dwell time within the bonder was about 4 seconds. The resultant web had a basis weight as calculated above of 48.8 grams per square meter (gsm). During the bonding process, the samples were compressed from an initial thickness of approximately 200 mils (0.518 cm) to a final thickness of approximately 100 mils (0.259 cm) at a pressure of 689 dynes/square cm. The web was wound up on a roll and then transferred to an apparatus similar to that shown in FIG. 1 of the drawings.

The pulp sheet was formed using conventional pulp sheet forming equipment. Into the repulper there was placed on a weight percent basis not counting the water in the repulper: 49.5 percent Longlac northern softwood fibers available from the Kimberly-Clark Corporation, 49.5 percent Coosa River 54 southern softwood fibers also available from the Kimberly-Clark Corporation and 1.0 percent PA727 Arosurf chemical debonder from the Witco/Sherex Chemical Company, Inc. of Dublin, Ohio. The pulp fibers and debonder were mixed as a slurry for approximately 15 minutes. A wet laid pulp sheet was formed from the slurry having a basis weight of approximately 75 grams per square meter. The nonwoven web was brought into the forming process under the wet laid pulp sheet and the combination was passed through a hydroentangling apparatus which included four manifolds. The pulp sheet and nonwoven were supported on a 100 mesh stainless steel forming wire with the nonwoven positioned adjacent the wire. The line speed through the hydroentangling apparatus was 6.1 meters per minute (20 feet per minute). Each manifold was fitted with a single row of water jets with a hole density of 11.8 holes per centimeter (30 holes per inch) and an overall width in the cross machine direction of approximately 46 centimeters. The hole diameter of each of the holes in the water jet was 0.01778 centimeters (cm) (0.007 inches). Each of the manifolds was adjusted for its individual pressure. The upstream manifold was adjusted to have a pressure of 250 pounds per square inch gauge (1724 kilopascals) and the other three manifolds were all adjusted to a pressure of 400 pounds per square inch gauge (2758 kilopascals). As the entangled composite exited the hydroentangling apparatus, the nonwoven side of the composite was sprayed with a surfactant solution which contained 80 liters of deionized water, 240 grams of n-hexanol and 600 grams of Y-12488 organosiloxane surfactant from the Union Carbide Chemical and Plastics Company of Danbury, Conn. The mixture was stirred in a vat at room temperature for 10 minutes and then sprayed onto the nonwoven side of the composite so as to impart to the overall web a concentration of 1.0 percent by weight based upon the total weight of the composite web. Next the composite web was sent through a through-air dryer set to a drying temperature of 149° C. (300° F.). The dwell time within the dryer was approximately 23 seconds. The resultant material had a basis weight of approximately 125 grams per square meter.

Sample 1b was the same nonwoven layer and the same pulp sheet. The only difference was in the hydroentangling of the pulp sheet. With sample 1a the pulp sheet was hydroentangled into the nonwoven layer. This caused a realignment of the fibers in the pulp sheet. To simulate this effect in samples 1b, 2b, 3b and 4b, the same pulp sheets as were used in respective samples 1a, 2a, 3a and 4a were sent through the hydroentangling process by themselves using only three of the manifolds each set to a pressure of 250 psig (1724 kilopascals). The pressure was reduced because it was found that at the same pressure as was used with respect to the "a" samples, the pulp fibers of the pulp sheet would embed themselves in the foraminous forming wire. Once the pulp sheets had been hydroentangled and dried, they were placed on top of the nonwovens of the respective examples and the testing was performed.

Sample 1c used the same materials as sample 1b, the only difference being that the two layers of material were adhesively attached to one another. The adhesive add-on was approximately 25 gsm.

Basis weight, fluid intake rates, cup crush loads, cohesion force and demand absorbency rates for the composites were measured and are reported in Tables 1 and 2.

The composite material produced in this manner (sample 1a) had a combination of good fluid properties. The lofty nonwoven side of the composite provided an intake/surge functionality which is important when the material is used as an intake portion of a personal care absorbent article such as a sanitary napkin. In such contexts the nonwoven acts to readily absorb fluids discharged from the body, hold them and then transfer them to the pulp portion of the composite. The pulp portion of the composite provides both retention capacity and the ability to directionally distribute fluids along the machine direction of the material due to the fiber alignment of the pulp fibers during the hydroentangling process. Another important factor contributing to the fluid distribution is the zone in which the pulp fibers are entangled with the nonwoven fibers. This area of intimate contact/interface improves fluid transport from the nonwoven surge/distribution layer into the pulp distribution/absorbent layer.

TABLE 1

Intake rates for Examples 1–5

|  | Intake Rate (cc/min) |
|---|---|
| Example 1a | 6.28 |
| Example 2a | 2.04 |
| Example 3a | 3.74 |
| Example 4a | 2.07 |
| Example 5 | 1.34 |

TABLE 2

Data for Examples 1a, 1b, and 1c

|  |  | Example 1a | Example 1b | Example 1c |
|---|---|---|---|---|
| Basis Weight | (g/m2) | 127.38 | 118.70 | 143.59 |
| Cohesion | (kg/in2) | 1.88 | 0.00 | 0.70 |
| Cup Crush | (kg) | 646 | 422 | 859 |
| Demand Absorbency | (g/min) | 3.17 | 0.29 | 0.25 |

Examples with a "b" were plies of material, not entangled
Examples with a "c" were adhesively bonded Example 2

In Example 2a a two layer composite was formed using a bonded carded web and a pulp sheet. The bonded carded web was a through-air bonded carded web which included on a weight percent basis based upon the total weight of the web: 25 percent 1.5 denier rayon staple fibers having a length of 39.7 millimeters, 35 percent 3.0 denier polyethylene sheath/polyester core bicomponent fibers having a length of 38 millimeters and 40 percent 6.0 denier polyester staple fibers having a length of 38 millimeters. The rayon staple fibers were obtained from Courtaulds North America, Inc. of New York, N.Y. and were designated as being from lot number 18543. The bicomponent fibers were obtained from the BASF Wyandotte Corporation of Parsippany, N.J. and were designated as being from merge 1-1039. The polyester staple fibers were obtained from the Hoechst Celanese Corporation of Spartanburg, S.C. and were designated T-295.

The staple fibers were all sent through an opener twice and were uniformly mixed together before being carded into a web at a line speed of 15.24 meters per minute (50 feet per minute). Once the web had been formed, it was then sent through a through-air bonder (drum type) with an air temperature of 163° C. (325° F.). The dwell time within the bonder was between about 3 and about 4.5 seconds. The resultant web had a basis weight as calculated above of 50 grams per square meter (gsm). The web was wound up on a roll and then transferred to an apparatus similar to that shown in FIG. 1 of the drawings.

The 75 gsm pulp sheet was the same as that used in Example 1. The pulp sheet and the bonded carded web were brought together and entangled under the same conditions as were used in Example 1. The 125 gsm composite material had the same good properties as the composite in Example 1.

Sample 2b used the same materials as sample 2a with the same modifications as outlined above with respect to sample 1b. Sample 2c was made from the same materials as sample 2b. Adhesive add-on for sample 3c was approximately 20 gsm.

Basis weight, fluid intake rates, cup crush loads, cohesion force and demand absorbency rates for the composites were measured and are reported in Tables 1 and 3.

TABLE 3

Data for Examples 2a, 2b, and 2c

| | | Example 2a | Example 2b | Example 2c |
|---|---|---|---|---|
| Basis Weight | (g/m2) | 121.91 | 121.24 | 141.66 |
| Cohesion | (kg/in2) | 5.61 | 0.00 | 4.17 |
| Cup Crush | (kg) | 426 | 423 | 694 |
| Demand Absorbency | (g/min) | 1.63 | 0.11 | rate <0.1 |

Examples with a "b" were plies of material, not entangled
Examples with a "c" were adhesively bonded Example 3

In Example 3a a 75 gram per square meter pulp sheet was used which had the same fiber and debonder formulation as in Example 2. The nonwoven web into which it was integrated was in this case a two layer bonded carded web having a total basis weight of 50 grams per square meter. The top layer of the nonwoven web was a 17 gram per square meter through-air bonded carded web made entirely from 1.8 denier polyethylene sheath/polyester core bicomponent fibers having a length of 38 millimeters. These fibers were obtained from the BASF Wyandotte Corporation of Parsippany, N.J.

The bottom layer of the two layer bonded carded web was a 33 gram per square meter homogeneous blend of 30 weight percent 1.5 denier rayon fibers (the same as were used in Example 2) and 70 percent 3.0 denier polyethylene sheath/polyester core bicomponent fibers (again the same as were used in Example 2). The weight percents were based upon the total weight of the bottom layer.

The two layers were through-air bonded together using the same equipment as in Example 2. The bonding temperature was 163° C. and the dwell time within the through-air bonder was approximately 3 to 4.5 seconds.

The wet pulp sheet was brought into the hydroentangling apparatus on top of the two layer bonded carded web. The bonded carded web was positioned such that the pulp sheet contacted the bottom layer. Unlike the previous examples, only three of the four manifolds were used in this example. All three of the manifolds were adjusted to a gauge pressure of 400 psig (2758 kilopascals). The line speed remained the same at 6.1 meters per minute.

After the hydroentangling, the nonwoven side of the composite was sprayed with the same surfactant solution as was used in Examples 1 and 2 and the application rate was also the same. The composite web was then dried in the same fashion as the previous samples at a temperature of 138° C.

Samples 3b and 3c were made in the same fashion as their counterpart samples in the previous examples using the same materials as in sample 3a. The pulp sheet was hydroentangled in the same manner as samples 1b and 2b. Adhesive add-on for sample 3c was approximately 18 gsm.

Basis weight, fluid intake rates, cup crush loads, cohesion force and demand absorbency rates for the composites were measured and are reported in Tables 1 and 4.

The resultant composite material according to the present invention (sample 3a) had one surface which was very soft to the touch due to the use of the 1.8 denier bicomponent fibers. This side of the material was ideally suited for use as the body-contacting surface of a personal care absorbent article. The other surface of the laminate was rich in pulp fibers and therefore could act as a good absorbent. In between the two surfaces the "bottom layer" of the two layer bonded carded web could provide an additional functionality to the overall composite by acting as a surge layer to quickly desorb the body contacting portion of the laminate and then hold the fluid until such time as the pulp fibers could fully absorb the insulted fluid. By using the hydroentangling process, there was sufficient intermixing of pulp and nonwoven matrix fibers at the interface of the two materials to support this fluid transport process. Consequently, this laminate when coupled with a liquid impervious material adjacent the pulp side could be used as, for example, a thin pantiliner. Furthermore, unlike layered products or products which have the layers adhesively attached to one another, this entangled structure had increased fluid handling and a decreased ply separation as shown by the data in Tables 1 and 4.

TABLE 4

Data for Examples 3a, 3b, and 3c

| | | Example 3a | Example 3b | Example 3c |
|---|---|---|---|---|
| Basis Weight | (g/m2) | 130.20 | 131.24 | 149.03 |
| Cohesion | (kg/in2) | 2.22 | 0.00 | 1.48 |
| Cup Crush | (kg) | 740 | 658 | 972 |

TABLE 4-continued

Data for Examples 3a, 3b, and 3c

|  | Example 3a | Example 3b | Example 3c |
|---|---|---|---|
| Demand (g/min) Absorbency | 2.20 | 0.26 | 0.25 |

Examples with a "b" were plies of material, not entangled
Examples with a "c" were adhesively bonded Example 4

In Example 4a a two layer composite was produced using a spunbond web and a pulp sheet. The spunbond web was a through-air bonded bicomponent fabric which was produced as described in U.S. Pat. No. 5,382,400. The approximately 2 to 3 denier bicomponent spunbond fibers were 50% polypropylene and 50% polyethylene (on a weight percent basis) arranged in a side-by-side configuration. A 34 grams per square meter fabric of crimped bicomponent fibers was produced, through air bonded and delivered to the entangling process.

The pulp portion of the composite was produced essentially as in Example 1 except for the basis weight, which was reduced to 70 grams per square meter. To this pulp sheet was added the bicomponent spunbond web. The entangling process was as described in Example 1, however, this composite was produced with three manifolds of water jets adjusted to 2758 kilopascals (kPa).

Using the same materials as in sample 4a, samples 4b and 4c were also prepared. Add-on for the adhesive in sample 4c was approximately 11 gsm.

Basis weight, fluid intake rates, cup crush loads, cohesion force and demand absorbency rates for the composites were measured and are reported in Tables 1 and 5.

TABLE 5

Data for Examples 4a, 4b, and 4c

|  |  | Example 4a | Example 4b | Example 4c |
|---|---|---|---|---|
| Basis Weight | (g/m2) | 102.93 | 101.69 | 112.88 |
| Cohesion | (kg/in2) | 4.17 | 0.00 | 2.63 |
| Cup Crush | (kg) | 665 | 356 | 535 |
| Demand Absorbency | (g/min) | 1.58 | 0.19 | 0.38 |

Examples with a "b" were plies of material not entangled
Examples with a "c" were adhesively bonded Example 5

Example 5 was a pulp sheet control made to measure and compare the fluid intake rate of pure hydroentangled pulp (See Table 1). The pulp sheet was 75 gsm and was made in the same fashion as the other pulp sheets. Hydroentangling was done using three manifolds adjusted to a pressure of 250 psig (1724 kPa).

A comparison of the intake rate data in Table 1 illustrates the benefits of the addition of a matrix fiber (nonwoven web) to a pulp sheet. The matrix fibers provide a nonwoven rich side to the composite which can more quickly absorb available fluid as compared with the slower pulp sheet in Example 5. This rapid intake eliminates free fluid which could by-pass the absorbent and cause premature product failure.

Tables 2 through 5 illustrate three methods of adding together matrix and pulp sheet fibers. In each Example, the "a" sample represented the entangled structure according to the present invention while the "b" sample contained no bonding or entanglement between the layers of material. The "c" sample supplanted the entangling of the two layers with adhesive attachment. Cohesion measures the attachment of the components and was highest in the entangled materials, samples "a". Increasing the adhesive level of samples "c" would increase the cohesion but as can be seen from the cup crush data, the adhesively bonded samples were already much stiffer than the entangled samples.

Figure 7:
Figure 8:
Figure 9:
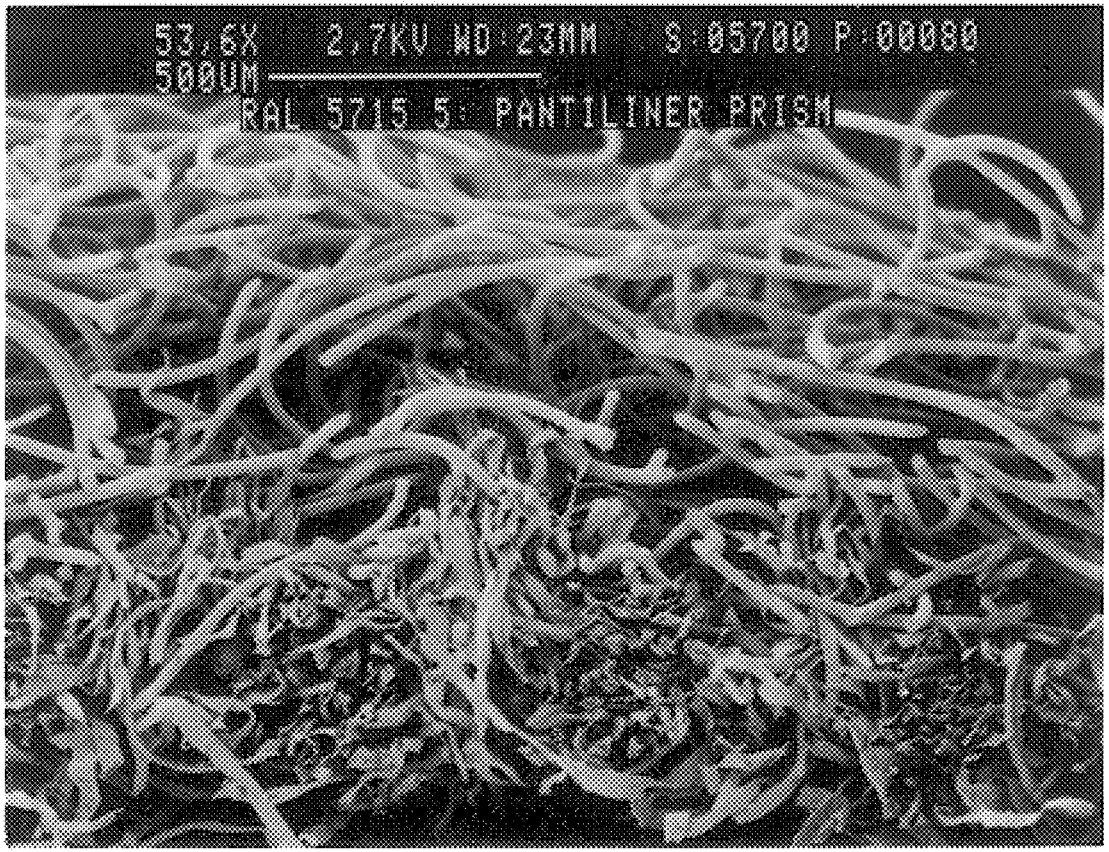
FIG. 9 is a photomicrograph of a material according to the present invention.

By far the most significant impact off entangling can be seen in the demand absorbency data. As these results clearly indicate, the entangled structures can absorb fluid at a much faster rate than alternative structures. This is believed to be due to the enhanced fluid pathways provided by the pulp fibers which extend into the matrix fibers of the composite. Referring to FIGS. 7, 8 and 9, the photomicrographs show how the ribbon-like pulp fibers can be seen projecting up into the low density matrix fibers. When samples are layered or adhesively attached together, the pulp fibers do not extend into the matrix fibers. In the "b" samples there was a layer of air between the pulp fiber layer and the matrix fiber layer. In the "c" samples there was an adhesive layer between the layers of pulp fibers and matrix fibers. In both cases the net effect was a limited pathway for liquid flow from one portion of the structure to the other. This was proven by the low demand absorbency data results for the non-hydroentangled samples.

The excellent demand absorbency data would seem to indicate that full integration of the pulp fibers and matrix fibers would maximize results. This is not the case, however, since there must be a balancing of all properties. By providing a pulp-rich side to the composite there is believed to be provided a fluid storage capability which can be removed from the wearer. In contrast, by providing a matrix fiber-rich side to the composite, a surface can be provided which can be aesthetically pleasing and which also maximizes fluid intake. This side can be used as the body facing surface of the product either alone or as shown in Example 3 with an additional layer of matrix fibers which are smaller in diameter and therefore more pleasing to the touch.

Figure 10:
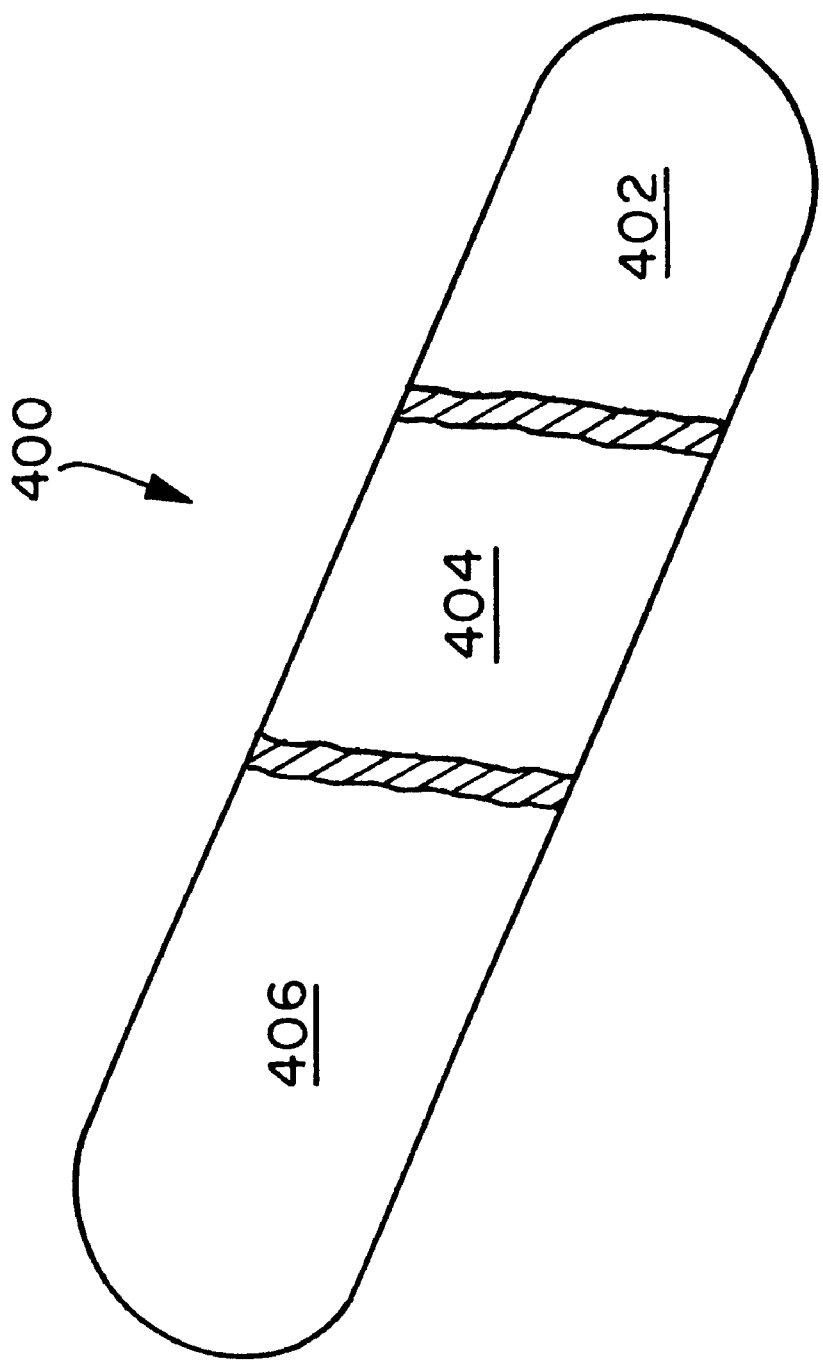
FIG. 10 is a cut-away perspective view of a personal care absorbent article, in this case a pantiliner, employing a composite according to the present invention.

The materials of the present invention can be used in a wide variety of applications not the least of which is in personal care absorbent articles. Personal care absorbent articles include, for example, diapers, training pants, incontinence devices, bandages and feminine hygiene products such as sanitary napkins and pantiliners. Referring to FIG. 10 of the drawings there is shown a pantiliner 400. Pantiliners are a much thinner version of sanitary napkins which are worn on light flow days and/or in addition to tampons by many women. Most personal care absorbent articles such as the pantiliner 400 include a backing sheet 402 which is usually liquid impervious and an absorbent core 404 such as wood pulp fibers with or without superabsorbent admixed therewith. In addition, such articles can optionally include a body side liner or top sheet 406 for placement adjacent the wearer's skin. The two layer hydroentangled materials, such as those described in Examples 1, 2 and 4, can be used as the absorbent core 404 in conjunction with the backing sheet 402 to form, for example, a pantiliner 400. The pulp-rich side of the composite is positioned adjacent the backing sheet 402 and the matrix-rich side of the composite is positioned adjacent the wearer. As a result, the matrix-rich side will function to readily take in fluids which will then be transferred to the pulp-rich side of the absorbent composite via the hydroentangled interior portion. In so doing, the fluid is removed from the vicinity of the wearer's skin and is stored in the pulp fibers adjacent to backing sheet.

It is also possible to utilize a multilayer material such as the composite according to the present invention described in Example 3 as the absorbent core 404. The same functioning occurs with the additional benefit that the smaller denier fibers in the layer opposite that of the pulp-rich side are much softer and more comfortable to the touch thereby yielding a more aesthetically pleasing product. As a result, it is generally not necessary to use an additional layer as a body side liner or top sheet 406 in the construction of the pantiliner 400 though one may be used if so desired.

Having thus described the invention in detail it should be apparent that various modifications and changes can be made in the present invention without departing from the spirit and scope of the following claims.

We claim:

1. An entangled nonwoven composite having a fluid intake exterior surface and a fluid retention exterior surface separated by an interior portion, said composite including from about 20 to 70 weight percent absorbent fibers and from 30 to about 80 weight percent matrix fibers based upon the total weight of said composite, said fluid intake exterior surface comprising essentially matrix fibers and said retention exterior surface comprising essentially absorbent fibers, said interior portion containing a mixture of said absorbent fibers and said matrix fibers entangled with one another, said composite having a fluid intake rate of about 2 cubic centimeters per minute or greater, a cohesion value of about 1.5 kilograms per $in^2$ or greater, a cup crush load value of about 1000 grams or less and a demand absorbency rate of one gram per minute or greater.

2. The composite of claim 1 wherein said composite includes about 50 to about 60 percent absorbent fibers and about 40 to about 50 percent matrix fibers based upon the total weight of said composite.

3. The composite of claim 1 wherein said composite further includes a fibrous nonwoven web including a plurality of matrix fibers positioned adjacent to and in contact with said fluid intake exterior surface.

4. The composite of claim 3 wherein said fibrous nonwoven web in contact with said fluid intake surface includes matrix fibers with diameters which are smaller than said matrix fibers in said top sheet.

5. The composite of claim 1 wherein said absorbent fibers contain a wet strength resin.

6. The composite of claim 3 wherein said absorbent fibers contain a wet strength resin.

7. The composite of claim 1 wherein said absorbent fibers contain a superabsorbent admixed therewith.

8. The composite of claim 3 wherein said absorbent fibers contain a superabsorbent admixed therewith.

9. A personal care absorbent article comprising a backing sheet and an absorbent core, said absorbent core comprising the composite of claim 1.

10. A personal care absorbent article comprising a backing sheet and an absorbent core, said absorbent core comprising the composite of claim 3.

11. The personal care absorbent article of claim 9 wherein said article is a pantiliner.

12. The personal care absorbent article of claim 10 wherein said article is a pantiliner.

* * * * *